(12) United States Patent
Newmark et al.

(10) Patent No.: US 7,067,159 B2
(45) Date of Patent: *Jun. 27, 2006

(54) METHODS FOR TREATING PROSTATE CANCER WITH HERBAL COMPOSITIONS

(75) Inventors: Thomas Newmark, St. Louis, MO (US); Paul Schulick, Brattleboro, VT (US); Aaron Katz, New York, NY (US)

(73) Assignee: New Chapter, Inc., Brattleboro, VT (US)

( * ) Notice: Subject to any disclaimer, the term of this patent is extended or adjusted under 35 U.S.C. 154(b) by 170 days.

This patent is subject to a terminal disclaimer.

(21) Appl. No.: 10/728,087

(22) Filed: Dec. 5, 2003

(65) Prior Publication Data

US 2005/0123631 A1     Jun. 9, 2005

(51) Int. Cl.
*A01N 65/00*    (2006.01)

(52) U.S. Cl. ............... 424/725; 424/729; 424/745; 424/756

(58) Field of Classification Search ............ None
See application file for complete search history.

(56) References Cited

U.S. PATENT DOCUMENTS

| | | | |
|---|---|---|---|
| 5,344,991 A | 9/1994 | Reitz et al. | |
| 5,380,738 A | 1/1995 | Norman et al. | |
| 5,393,790 A | 2/1995 | Reitz et al. | |
| 5,434,178 A | 7/1995 | Talley et al. | |
| 5,466,823 A | 11/1995 | Talley et al. | |
| 5,474,995 A | 12/1995 | Ducharme et al. | |
| 5,510,368 A | 4/1996 | Lau et al. | |
| 6,261,607 B1 * | 7/2001 | Newmark et al. | 424/727 |
| 6,387,416 B1 * | 5/2002 | Newmark et al. | 424/725 |
| 6,469,040 B1 | 10/2002 | Seibert et al. | |
| 6,488,957 B1 * | 12/2002 | Koumarianos | 424/439 |
| 6,534,540 B1 | 3/2003 | Kindness et al. | |
| 6,541,045 B1 * | 4/2003 | Charters et al. | 424/737 |

FOREIGN PATENT DOCUMENTS

| | | |
|---|---|---|
| WO | WO 94/13635 | 6/1994 |
| WO | WO 94/15932 | 7/1994 |
| WO | WO 94/20480 | 9/1994 |
| WO | WO 94/26731 | 11/1994 |
| WO | WO 94/27980 | 12/1994 |
| WO | WO 95/00501 | 1/1995 |
| WO | WO 95/15316 | 6/1995 |
| WO | WO 96/03387 | 2/1996 |
| WO | WO 96/03388 | 2/1996 |
| WO | WO 96/06840 | 3/1996 |
| WO | WO 96/25405 | 8/1996 |

OTHER PUBLICATIONS

Chandrasekharan, N.V. et al. "COX-3, a cyclooxygenase-1 variant inhibited by acetaminophen and other analgesic/antipyretic drugs: Cloning, structure, and expression", *PNAS*, vol. 99 (21), pp. 13926-13931, 2002.

* cited by examiner

*Primary Examiner*—Christopher R. Tate
(74) *Attorney, Agent, or Firm*—Nath & Associates PLLC; Gary M. Nath; Jerald L. Meyer (57) ABSTRACT

The inventive subject matter relates to methods for treating prostate cancer, comprising administration of a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

35 Claims, 5 Drawing Sheets

METHODS FOR TREATING PROSTATE CANCER WITH HERBAL COMPOSITIONS

BACKGROUND OF THE INVENTIVE SUBJECT MATTER

1. Field of the Inventive Subject Matter

The present inventive subject matter relates to novel methods for treating prostate cancer, comprising administration of a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

2. Background

Prostate Cancer. Prostate cancer is the third most common cause of death from cancer in men of all ages and is the most common cause of death from cancer in men over 75 years old. Prostate cancer is rarely found in men younger than 40. Men at higher risk include black men older than 60, farmers, tire workers, painters, and men exposed to cadmium. The lowest incidence occurs in Japanese men and vegetarians. The cause of prostate cancer is unknown, although some studies have shown a relationship between high dietary fat intake or increased testosterone levels.

Prostate cancer is a serious and often life-threatening condition. Prostate cancer, which is characterized by rapidly-proliferating cell growth, continues to be the subject of worldwide research efforts directed toward the identification of therapeutic agents which are effective in the treatment thereof. Effective therapeutic agents prolong the survivability of the patient, inhibit the rapidly-proliferating cell growth associated with the disease, or effect a regression of the disease. Research in this area is primarily focused on identifying agents which are therapeutically effective in humans and other mammals.

With prostate cancer, as with all solid tumors, it is the metastatic encroachment of the tumor on other vital function that causes the demise of the patient. Approximately 10% of patients are diagnosed initially with metastatic disease. Ultimately, 30–40% of patients with this cancer will develop metastatic disease. Once metastasis occurs, the cancer follows a relentless progression unless interrupted by effective treatment. Prostate cancers are classified based on their aggressiveness and how different they are from the surrounding prostate tissue. There are several different ways to classify tumors; one of the more common is the Whitmore-Jewett system, in which tumors are rated as follows:

A: tumor is unable to be felt on physical examination, and is usually detected by accident after prostate surgery done for other reasons.

B: tumor is confined to the prostate and usually detected by physical examination or PSA testing.

C: extension of tumor beyond the prostate capsule without spread to lymph nodes.

D: cancer has metastasized to regional lymph nodes or other parts of the body, such as the bone and lungs for example.

With the advent of Prostate Specific Antigen (hereinafter "PSA") testing, most prostate cancers are now found before they cause symptoms. The symptoms listed below are possible indicators of prostate cancer: urinary hesitancy, urinary dribbling, urinary retention, pain with urination, pain with ejaculation, lower back pain, pain with bowel movement, excessive urination at night, incontinence, bone pain or tenderness, hematuria, abdominal pain, anemia, weight loss, and lethargy.

The appropriate treatment of prostate cancer is often controversial. Treatment options vary based on the stage of the tumor. In the early stages, surgical removal of the prostate and radiation therapy may be used to eradicate the tumor. Metastatic cancer of the prostate may be treated by hormonal manipulation, reducing the levels of testosterone by drugs or removal of the testes, or by chemotherapy.

Surgical removal of the prostate has several possible complications, including impotence and urinary incontinence. Removal of the testes alters hormone production and may be recommended for metastatic cancer, and has possible complications including loss of testosterone production, leading to problems with sexual function, osteoporosis, and loss of muscle mass. Radiation therapy has possible complications including loss of appetite, fatigue, skin reactions such as redness and irritation, rectal burning or injury, diarrhea, cystitis, and blood in the urine. Hormonal manipulation, which is mainly used to relieve symptoms without curing the prostate cancer, has possible complications including nausea and vomiting, hot flashes, anemia, lethargy, osteoporosis, reduced sexual desire, liver problems, diarrhea, enlarged breasts, and erectile dysfunction, along with the obvious lack of treatment of the disease itself. Chemotherapy, using medications such as mitoxantrone, prednisone, paclitaxel, docetaxel, estramustine, and adriamycin, has possible complications which are numerous and specific to a given chemotherapy drug.

Sufferers of prostate cancer often experience significant lifestyle changes, including disrupted sexual desire or performance on either a temporary or permanent basis; impotence; extensive monitoring for progression of the disease; stress of illness; and urinary incontinence. Thus, there is a continuing need for alternative treatments for prostate cancer and for improved treatments for prostate cancer.

Cyclooxygenase Inhibitors. Cyclooxygenase is an enzyme-protein complex with a variety of biochemical actions. There are at least three primary COX isoenzymes, COX-1, COX-2, and COX-3. COX-1 is a constitutive enzyme, produced at a reasonably consistent level at all times. It plays an important role in, for example, gastrointestinal protection, kidney function, and the aggregation of blood platelets. COX-2 production is not constant; it varies depending on signals from various biochemical catalysts. For example, in the case of arthritis inflammation and pain, COX-2 responds to tissue damage by oxidizing arachidonic acid, creating prostaglandins which in turn produce local inflammation. COX-3 has been identified relatively recently (Chandrasekharan, et al., PNAS U.S.A., 99(21):13926–31 (2002)). In humans, COX-3 mRNA is expressed most abundantly in the cerebral cortex and heart tissues. COX-3 activity is selectively inhibited by analgesic/antipyretic drugs. It has been suggested that inhibition of COX-3 could represent a mechanism by which these drugs decrease pain and possibly fever.

Prostaglandins play a major role in the inflammatory process and the inhibition of prostaglandin production, especially production of $PGG_2$, $PGH_2$, and $PGE_2$, has been a common target of anti-inflammatory drug discovery. However, common non-steroidal anti-inflammatory drugs (hereinafter "NSAIDs") that are active in reducing the prostaglandin-induced pain and swelling associated with the inflammation process are also active in affecting other prostaglandin-regulated processes not associated with the inflammation process.

NSAIDs have been found to prevent the production of prostaglandins by inhibiting enzymes in the human arachidonic acid/prostaglandin pathway, including the cyclooxygenase enzymes. Traditional non-steroidal anti-inflammatory drugs, such as aspirin, work by inhibiting both COX-1 and COX-2. Thus, non-specific NSAIDs can have a damaging effect on the gastrointestinal tract, kidneys, and liver; blocking COX-1 can make the stomach lining more vulnerable, and reduced thromboxane production thins the blood, making gastrointestinal hemorrhage more likely, and may cause inadequate regulation of cellular immune functions and the secretion of various cytokines. The use of high doses of most common NSAID's can produce severe side effects, including life threatening ulcers, that limit their therapeutic potential.

COX-2 is associated with inflammation and provides a viable target of inhibition which more effectively reduces inflammation and produces fewer and less drastic side effects. Thus, researchers have been motivated to develop selective COX-2 inhibitors to reduce inflammation and relieve pain without the gastrointestinal damage brought on by inhibiting COX-1. In addition, the current scientific understanding in the art suggests that COX-2 inhibition may serve an important function in promoting normal cell growth in the colon, pancreas, breast tissue, and other organ systems.

Some compounds which selectively inhibit cyclooxygenase-2 have been described in U.S. Pat. Nos. 5,380,738, 5,344,991, 5,393,790, 5,434,178, 5,474,995, 5,510,368 and WO documents WO96/06840, WO96/03388, WO96/03387, WO96/25405, WO95/15316, WO94/15932, WO94/27980, WO95/00501, WO94/13635, WO94/20480, and WO94/26731.

Drugs such as valdecoxib, celecoxib, and rofecoxib are intended to selectively inhibit COX-2 with minimal effect on COX-1. However, despite the emphasis on COX-2 inhibition, even these drugs appear to have serious long term side effects, such as the breakdown in digestive protective mucus and prevention of normal healing processes. There is thus a continuing need for more specific and non-specific COX-2 inhibitors which avoid side effects associated with COX-1 inhibition.

Natural COX-2 Inhibitors. Several herbs have been found to inhibit the COX-2 enzyme. For example, holy basil has been found to possess significant anti-inflammatory properties and is capable of blocking both the cyclooxygenase and lipoxygenase pathways of arachidonate metabolism. Ursolic acid and oleanolic acid, two of the recognized phytonutrients of holy basil, have been found to have a significant COX-2 inhibitory effect.

Similarly, shogaols and gingerols, pungent components of ginger, have been found to inhibit cyclooxygenase. Eugenol, another active constituent of several medical herbs, has also been found to be a 5-lipoxygenase inhibitor and to possess potent anti-inflammatory and/or anti-rheumatic properties.

*Scutellaria baicalensis* also has been found to inhibit the COX-2 enzyme. According to the USDA database, green tea contains six constituents having cyclooxygenase-inhibitor activity. According to the Napralert database, green tea contains fifty one constituents having anti-inflammatory activity. The polyphenols in green tea were found to cause a marked reduction in COX-2. Flavan-3-ol derivatives (+)-catechin, also present in green tea, have been reported to be COX-1 and COX-2 inhibitors. In addition, salicylic acid, another constituent of green tea, also has been found to be a COX-2 inhibitor.

Berberine, found in barberry and Chinese goldthread, has also been found to inhibit COX-2 without inhibiting COX-1 activity.

In U.S. Pat. No. 6,387,416, Applicants disclosed the inventive compositions and their use for reducing inflammation. The contents of U.S. Pat. No. 6,387,416 are hereby incorporated by reference in their entirety. Surprisingly, as discussed in greater detail below, it has been determined that the inventive compositions are useful for treating prostate cancer as well.

Use of COX-2 Inhibitors for Treating Cancer. It has been postulated that COX-2 inhibitors may be useful for treating cancer. Yet only a very few patents actually disclose the use of COX-2 inhibitors for treating any cancers. In U.S. Pat. No. 5,466,823 to Talley, et al., (Pyrazol-1-yl)benzene sulfonamides are disclosed as inhibitors of cyclooxygenase-2, and for use in the treatment of inflammation, arthritis, and pain, and as being useful for preventing colon cancer. However, their use for actually treating colon cancer or for treating or preventing other neoplasias is not disclosed.

U.S. Pat. No. 6,469,040 to Seibert, et al., discloses a method of using a specific, disclosed class of cyclooxygenase-2 inhibitor derivatives in preventing and treating epithelial cell neoplasia in a subject.

U.S. Pat. No. 6,534,540 to Kindness, et al., discloses a combination of the proprietary HMG-COA reductase inhibitor lovastatin and the proprietary COX-2 inhibitor rofecoxib for the treatment of cancer, especially prostate cancer, and a method of treatment of cancer, especially prostate cancer, by that combination.

Based on the limited body of art disclosing the use of COX-2 inhibitors for treating any cancer, and the need for effective treatments for prostate cancer in particular, it is apparent that there is a great and immediate need for new COX-2 inhibitors for treating prostate cancer. This need is met by the inventive methods and compositions, which treat prostate neoplasias without significant side effects.

SUMMARY OF THE INVENTIVE SUBJECT MATTER

The present inventive subject matter relates to a method for treating prostate neoplasia in a subject, comprising the step of administering an effective amount of a composition to said subject to treat or prevent said prostate neoplasia, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry, provided that said prostate neoplasia is not prostatic intraepithelial neoplasia.

The present inventive subject matter further relates to a method for treating at least one cancerous tumor of the prostate in a subject, comprising the step of administering an effective amount of a composition to said subject to treat said tumor, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

In addition, the present inventive subject matter is drawn to a method for treating side effects associated with prostate neoplasia in a subject, comprising the step of administering an effective amount of a composition to said subject to treat said side effects, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry, wherein said side effects are selected from the group consisting of disrupted sexual desire or performance on either a temporary or permanent basis, impotence, extensive monitoring for progression of the disease, stress of illness, and urinary incontinence.

DETAILED DESCRIPTION OF THE INVENTIVE SUBJECT MATTER

Definitions

The term "therapeutically effective amount" as used herein refers to that amount of the extract which will contribute to the cancer-treating ability of the composition.

The term "treating" as used herein refers to partial or total inhibition of the growth, spreading, or metastasis of prostate neoplasia, as well as partial or total destruction of the cancer cells. The term "treating" includes the reduction or elimination of prostate neoplasia, and also the reduction in the incidence of the disease.

The term "preventing" as used herein refers to either preventing the onset of prostate neoplasia, or preventing the onset of a preclinically evident stage of prostate neoplasia in individuals at risk. Also intended to be encompassed by this definition is the prevention of initiation for malignant cells, and the arrest or reversal of the progression of premalignant cells to malignant cells. "Preventing" also includes the prevention of growth or spreading of the prostate neoplasia. This includes prophylactic treatment of those at risk of developing a prostate neoplasia.

The term "supercritical gas" or "supercritical fluid" as used herein refers to a gas is that heated to a temperature critical point, over which the gas will maintain its gaseous state and not turn to a liquid regardless of pressure. A gas heated to a temperature above its critical point will become very dense on compression, so that its characteristics resemble those of a fluid, but will become liquid. Carbon dioxide is commonly used in applications requiring a supercritical fluid. The general properties of supercritical fluids and the general use of supercritical fluids in extraction processes are described in, e.g. Taylor, *Supercritical Fluid Extraction*, Wiley, 1996; McHugh and Krukonis, *Supercritical Fluid Extraction: Principles and Practice*, 2nd ed., Butterworth-Heinemann, 1994; and Williams and Clifford, *Supercritical Fluid Methods and Protocols*, Humana Press, 2000, the contents of which are incorporated by reference herein.

The term "supercritical extraction" as used herein refers to the technique in which hydrophobic compounds can be extracted from samples utilizing a supercritical fluid. The solvation power of a supercritical fluid is increased as the pressure and temperature are increased above their critical points, producing an effective solvent for the isolation of hydrophobic molecules.

The term "hydroalcoholic extraction" as used herein refers to to the technique in which hydrophillic compounds can be extracted from a sample utilizing a solution of alcohol and water, followed by evaporation of the solution to produce a extract consisting of dissolved solids.

The term "neoplasia" as used herein refers broadly to neoplastic, pre-malignant, and proliferative disease, including specifically benign, premalignant, or malignant neoplasms in individuals with or without any prior history or diagnosis of neoplastic, pre-malignant, or proliferative disease. The term "neoplasia" includes neoplasia that produce prostaglandins or express a cyclooxygenase, including both benign and cancerous tumors, growths, and polyps.

The term "prostate neoplasia" as used herein refers broadly to epithelial cancers, epitheliomas, carcinomas, sarcomas, or other malignant tumors or neoplasia of glandular origin in the prostate.

The term "subject" as used herein refers to any human or mammal subject who has a prostate neoplasia, preferably a human subject. For methods of prevention, the subject is any human or animal subject, preferably a human subject, who is at risk for developing an epithelial cell-derived prostate neoplasia. The subject may be at risk due to exposure to carcinogenic agents, being genetically predisposed to have a prostate neoplasia, and the like.

The term "cyclooxygenase-2 inhibitor" or "COX-2 inhibitor" as used herein refers to a compound or composition which is able to inhibit cyclooxygenase-2 without adverse inhibition of cyclooxygenase-1.

Methods for Treating Prostate Cancer

Although the occurrence rate of localized, latent forms of prostate cancer is consistent throughout the world, the occurrence of metastatic prostate cancer is much greater in western countries compared to eastern countries. This striking disparity suggests the involvement of environmental factors in the development of metastatic prostate cancer, and has prompted the initiation of several epidemiological studies which suggest a link between high fat diets and risk of metastatic prostate cancer. Both arachidonic acid and its precursor, linoleic acid, are present in significant quantities in animal fats and a variety of vegetable oils. Physiologically, these fatty acids are integral components of cellular membranes and also function as substrates for the production of an important group of potent, signaling lipids, termed eicosanoids. Eicosanoids are known to be involved in the initiation of the inflammatory response, fever production, regulation of blood pressure, blood clotting, control of reproductive processes and tissue growth, and regulation of the sleep/wake cycle. Additionally, these powerful mediators and the enzymes that produce them, cyclooxygenases (COX) and lipoxygenases (LO), are implicated in tumor development, progression, and metastasis.

The three main isoforms of cylooxygenase are COX-1, COX-2, and COX-3, and these enzymes are responsible for the production of the group of eicosanoids, prostaglandins.

The COX-1 isoform has many important housekeeping functions in the cell, and is therefore constitutively produced throughout the body. COX-2, however, is usually absent until induced by specific stimuli. It is therefore not surprising that COX-2 is implicated in the progression of many disease states, including cancer. COX-2 has been found to be present in elevated levels in a variety of cancers, including lung, colon, pancreatic, head and neck, and prostate cancer. As discussed above, COX-3 has only been relatively recently identified.

Regarding prostate cancer, it has been demonstrated that elevated levels of COX-2 are present in some tumor samples, and there is an increased level of COX-2 enzyme expression with disease progression. COX-2 activity and resultant prostaglandin production is also involved in tumor-induced angiogenesis, which we expect to be mediated by certain COX-2 inhibitors. Additionally, we expect that certain COX-2 inhibitors produce a re-initiation of apoptosis pathways, overcoming the anti-apoptotic factors secreted by cancer cells and leading to cell death.

The centuries old natural remedy of using white willow bark (*Salix alba*) to provide some pain relief led to the discovery of aspirin, and eventually, to the elucidation of its mechanism of action as a COX inhibitor. Based on this lead and other traditional Eastern medicinal practices, many researchers have looked to a variety of natural plant extracts and natural products for the discovery of both non-specific COX and specific COX-2 inhibitors. Some herbal extracts and natural products that have peaked interest amongst researchers include curcumin, ginger, holy basil, resveratrol, thundergod vine, and berberine from barberry and Chinese goldthread.

Applicants have developed a mixture comprised of herbal extracts, and the mixture has COX-2 inhibitory activity. Applicants' compositions are unique, in that they are prepared via a supercritical $CO_2$ extraction process. Unlike traditional solvent based extraction methods, supercritical $CO_2$ extraction allows the natural products in the herbs to be obtained without leaving chemical residues behind in the preparation.

Surprisingly, in addition to the anti-inflammatory action disclosed in U.S. Pat. No. 6,387,416, we have found that using the inventive compositions and methods produce COX-2 inhibition in prostate cancer cell lines. We also expect that the inventive methods induce apoptosis and inhibit cell growth in cancer cells which have deactivated apoptotic pathways.

The inventive subject matter is based on the discovery that a combination of certain herbs properly extracted and blended in appropriate proportions can used in treating prostate neoplasia. Thus, the present inventive subject matter relates to a method for treating prostate neoplasia in a subject, comprising the step of administering an effective amount of a composition to said subject to treat or prevent said prostate neoplasia, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry, provided that said prostate neoplasia is not prostatic intraepithelial neoplasia.

In one aspect, said composition is administered orally.

In another preferred embodiment, the orally administered composition is in the form of one or more capsules, one or more tablets, or one or more pills In another aspect, the composition comprises:

(A) from about 4.5% to about 7.5%, and more preferably from about 5.5% to about 6.5%, by weight of the hydroalcoholic extract of ginger;
(B) from about 5.5% to about 8.5%, and more preferably from about 6% to about 8%, by weight of the supercritical extract of ginger;
(C) from about 1.0% to about 1.5%, and more preferably from about 1.2% to about 1.4%, by weight of the supercritical extract of turmeric;
(D) from about 10.0% to about 16.0%, and more preferably from about 11.5% to about 14.5%, by weight of the supercritical extract of rosemary;
(E) from about 4.0% to about 6.0%, and more preferably from about 4.5% to about 5.5%, by weight of the supercritical extract of oregano;
(F) from about 10.0% to about 16.0%, and more preferably from about 11.5% to about 14.5%, by weight of the hydroalcoholic extract of turmeric;
(G) from about 5.5% to about 8.0%, and more preferably from about 6.0% to about 7.0%, by weight of the hydroalcoholic extract of rosemary;
(H) from about 10.0% to about 16.0%, and more preferably from about 11.5% to about 14.5%, by weight of the hydroalcoholic extract of holy basil;
(I) from about 10.0% to about 16.0%, and more preferably from about 11.5% to about 14.5%, by weight of the hydroalcoholic extract of green tea;
(J) from about 8.0% to about 12.0%, and more preferably from about 9.0% to about 11.0%, by weight of the hydroalcoholic extract of huzhang;
(K) from about 4.0% to about 6.0%, and more preferably from about 4.5% to about 5.5%, by weight of the hydroalcoholic extract of Chinese goldthread;
(L) from about 4.0% to about 6.0%, and more preferably from about 4.5% to about 5.5%, by weight of the hydroalcoholic extract of barberry; and
(M) from about 2.0% to about 3.0%, and more preferably from about 2.25% to about 2.75%, by weight of the hydroalcoholic extract of *Scutellaria baicalensis*.

The hydroalcoholic extract of ginger used in the present invention is preferably prepared as follows. The ginger rhizome, which is preferably cryogenically ground to preserve heat sensitive components, is subjected to supercritical extraction, preferably with carbon dioxide, to obtain: (i) an oil extract, referred to herein as "the supercritical extract" of ginger, containing delicate lipophilic components, and (ii) an oil-free residue. The oil-free residue is then extracted in a water/alcohol, preferably water/ethanol, mixture composed of 60–80 parts alcohol and 40–20 parts water. The alcohol/water liquid is then evaporated off, leaving a powdered extract residue, referred to herein as "the hydroalcoholic extract" of ginger.

In a preferred aspect, the weight ratio of the supercritical extract of ginger to the hydroalcoholic extract of ginger is from about 0.9:1 to about 1.4:1.

The supercritical extracts of ginger, rosemary, turmeric and oregano used in the present invention can be prepared according to known supercritical extraction methods, such as disclosed, e.g., in E. Stahl, K. W. Quirin, D. Gerard, Dense Gases for Extraction and Refining, Springer Verlag 4 1988, which is hereby incorporated by reference herein.

The hydroalcoholic extracts of rosemary, turmeric, holy basil, green tea, huzhang, Chinese goldthread, barberry and *Scutellaria baicalensis* used in the present invention can be prepared according to conventional hydroalcoholic extraction techniques. For example, the hydroalcoholic extracts can be prepared by extracting the plant portion in a water/ alcohol, preferably water/ethanol, mixture preferably composed of 60–80 parts alcohol and 40–20 parts water, and then evaporating off the water/alcohol liquid, leaving a powdered extract residue referred to herein as "the hydroalcoholic extract".

In yet another aspect, the weight ratio of the hydroalcoholic extract of turmeric to the supercritical extract of turmeric is from about 8:1 to about 12:1.

In an alternate aspect, the weight ratio of the supercritical extract of rosemary to the hydroalcoholic extract of rosemary is from about 1.6:1 to about 2.4:1.

In a still further aspect, the hydroalcoholic extract of ginger comprises from about 2.4% to about 3.6%, more preferably from about 2.7% to about 3.3%, and most preferably about 3.0%, by weight of pungent compounds.

In another aspect, the supercritical extract of ginger comprises from about 24% to about 36%, more preferably from about 27% to about 33%, and most preferably about 30%, by weight of pungent compounds; and from about 6.4% to about 9.6%, more preferably from about 7.2% to about 8.8%, and most preferably about 8%, by weight of zingiberene.

In a further aspect, the supercritical extract of turmeric comprises from about 36% to about 54%, more preferably from about 40.5% to about 49.5%, and most preferably about 45%, by weight of turmerones.

In another aspect, the supercritical extract of rosemary comprises from about 18.4% to about 27.6%, more preferably from about 20.7% to about 25.3%, and most preferably about 23%, by weight of total phenolic antioxidants.

In yet another aspect, the supercritical extract of oregano comprises from about 0.64% to about 0.96%, more preferably from about 0.72% to about 0.88%, and most preferably about 0.8%, by weight of total phenolic antioxidants.

In a still further aspect, the hydroalcoholic extract of turmeric comprises from about 5.6% to about 8.4%, more preferably from about 6.3% to about 7.7%, and most preferably about 7%, by weight of curcumin.

In another aspect, the hydroalcoholic extract of rosemary comprises from about 18.4% to about 27.6%, more preferably from about 20.7% to about 25.3%, and most preferably about 23%, by weight of total phenolic antioxidants.

In a further embodiment, the hydroalcoholic extract of holy basil comprises from about 1.6% to about 2.4%, more preferably from about 1.8% to about 2.2%, and most preferably about 2%, by weight of ursolic acid.

In a further aspect, the hydroalcoholic extract of green tea comprises from about 36% to about 54%, more preferably from about 40.5% to about 49.5%, and most preferably about 45%, by weight of polyphenols.

In another aspect, the hydroalcoholic extract of huzhang comprises from about 6.4% to about 9.6%, more preferably from about 7.2% to about 8.8%, and most preferably about 8%, by weight of resveratrol.

In another embodiment, the hydroalcoholic extract of Chinese goldthread comprises from about 4.8% to about 7.2%, more preferably from about 5.4% to about 6.6%, and most preferably about 6%, by weight of berberine.

In a further aspect, the hydroalcoholic extract of barberry comprises from about 4.8% to about 7.2%, more preferably from about 5.4% to about 6.6%, and most preferably about 6%, by weight of berberine.

In an alternate aspect, said composition comprises:

(A) from about 4.5% to about 7.5% by weight of the hydroalcoholic extract of ginger, wherein the extract comprises from about 2.4% to about 3.6% by weight of pungent compounds;

(B) from about 5.5% to about 8.5% by weight of the supercritical extract of ginger, wherein the extract comprises from about 24% to about 36% by weight of pungent compounds and from about 6.4% to about 9.6% by weight of zingiberene;

(C) from about 1.0% to about 1.5% by weight of the supercritical extract of turmeric, wherein the extract comprises from about 36% to about 54% by weight of turmerones;

(D) from about 10.0% to about 16.0% by weight of the supercritical extract of rosemary, wherein the extract comprises from about 18.4% to about 27.6% by weight of total phenolic antioxidants;

(E) from about 4.0% to about 6.0% by weight of the supercritical extract of oregano, wherein the extract comprises from about 0.64% to about 0.96% by weight of total phenolic antioxidants;

(F) from about 10.0% to about 16.0% by weight of the hydroalcoholic extract of turmeric, wherein the extract comprises from about 5.6% to about 8.4% by weight of curcumin;

(G) from about 5.5% to about 8.0% by weight of the hydroalcoholic extract of rosemary, wherein the extract comprises from about 18.4% to about 27.6% by weight of total phenolic antioxidants;

(H) from about 10.0% to about 16.0% by weight of the hydroalcoholic extract of holy basil, wherein the extract comprises from about 1.6% to about 2.4% by weight of ursolic acid;

(I) from about 10.0% to about 16.0% by weight of the hydroalcoholic extract of green tea, wherein the extract comprises from about 36% to about 54% by weight of polyphenols;

(J) from about 8.0% to about 12.0% by weight of the hydroalcoholic extract of huzhang, wherein the extract comprises from about 6.4% to about 9.6% by weight of resveratrol;

(K) from about 4.0% to about 6.0% by weight of the hydroalcoholic extract of Chinese goldthread, wherein the extract from about 4.8% to about 7.2% by weight of berberine;

(L) from about 4.0% to about 6.0% by weight of the hydroalcoholic extract of barberry, wherein the extract from about 4.8% to about 7.2% by weight of berberine; and (M) from about 2.0% to about 3.0% by weight of the hydroalcoholic extract of *Scutellaria baicalensis*;

and wherein said composition further comprises:

(i) the supercritical extract of ginger and the post-supercritical hydroalcoholic extract of ginger at a weight ratio of from about 0.9 to about 1.4 parts of supercritical extract per 1 part of post-supercritical hydroalcoholic extract;

(ii) the hydroalcoholic extract of turmeric and the supercritical extract of turmeric at a weight ratio of from about 8 to about 12 parts of hydroalcoholic extract per 1 part of supercritical extract; and (iii) the supercritical extract of rosemary and the hydroalcoholic extract of rosemary at a weight ratio of from about 1.6 to about 2.4 parts of supercritical extract per 1 part of hydroalcoholic extract.

In a preferred embodiment, the composition is administered in a daily dosage of at least about 700 mg.

In another aspect, the composition is administered on a daily basis for at least 4 weeks.

A still further aspect of the present inventive subject matter is drawn to a method for treating at least one cancerous tumor of the prostate in a subject, comprising the step of administering an effective amount of a composition to said subject to treat said tumor, said composition comprising therapeutically effective amounts of supercritical extracts of rosemary, turmeric, oregano and ginger; and therapeutically effective amounts of hydroalcoholic extracts of holy basil, ginger, turmeric, Scutellaria baicalensis, rosemary, green tea, huzhang, Chinese goldthread, and barberry.

In a still further embodiment of the present inventive subject matter, the at least one cancerous tumor is detected during surgery on the prostate of said subject, having not been felt by a physician on physical examination of said subject.

Yet still further, the present inventive subject matter includes the at least one cancerous tumor being confined to the prostate of said subject and is detected by a physician on physical examination of said subject.

An additional aspect of the present invention includes the cancer related to said at least one cancerous tumor extends beyond the prostate capsule of said subject, but has not spread to lymph nodes in said subject.

A further additional aspect of the present inventive subject matter is directed to the cancer related to said at least one cancerous tumor is metastasized to regional lymph nodes or other parts of said subject.

A preferred aspect of the present invention is directed to a method for treating side effects associated with prostate neoplasia in a subject, comprising the step of administering an effective amount of a composition to said subject to treat said side effects, said composition comprising therapeutically effective amounts of supercritical extracts of rosemary, turmeric, oregano and ginger; and therapeutically effective amounts of hydroalcoholic extracts of holy basil, ginger, turmeric, Scutellaria baicalensis, rosemary, green tea, huzhang, Chinese goldthread, and barberry, wherein said side effects are selected from the group consisting of disrupted sexual desire or performance on either a temporary or permanent basis, impotence, extensive monitoring for progression of the disease, stress of illness, and urinary incontinence.

A further preferred embodiment is drawn to the method wherein the side effect treated comprises disrupted sexual performance.

In an alternate aspect, the composition comprises an additional agent selected from the group consisting of antineoplastic agents, growth inhibiting agents, and nutrients.

There are large numbers of antineoplastic agents available in commercial use, in clinical evaluation and in pre-clinical development, which optionally are selected for treatment of prostate neoplasia by combination drug chemotherapy. Such antineoplastic agents fall into several major categories: antimetabolite agents, antibiotic-type agents, alkylating agents, hormonal agents, immunological agents, interferon-type agents, metallomatrix proteases, superoxide dismutase mimics or $\alpha_v \oplus_3$ inhibitors. Thus, in a preferred embodiment, said antineoplastic agent is selected from the group consisting of antimetabolite agents, antibiotic-type agents, alkylating agents, hormonal agents, immunological agents, interferon-type agents, metallomatrix proteases, superoxide dismutase mimics, and $\alpha_v \beta_3$ inhibitors.

One class of antineoplastic agents which may be used in combination with an inventive composition consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, and uricytin.

A second class of antineoplastic agents which may be used in combination with an inventive composition consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin, and trimelamol.

A third class of antineoplastic agents which may be used in combination with an inventive composition consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

A fourth class of antineoplastic agents which may be used in combination with an inventive composition consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Examples of radioprotective agents which may be used in the combination chemotherapy of this invention are AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron), and superoxide dismutase Enzon.

Thus, in a further preferred embodiment, said antineoplastic agent is selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-Al, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, stefflimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, and superoxide dismutase.

A benefit provided by the inventive compositions is the utilization of supercritical extraction, an innovative technology for extracting herbs at low temperature without the use of industrial chemical solvents. Such extraction process allows for the highest potency of active compounds in the extracts, as much as 250 times the potency of the original fresh plant material.

Set forth in Table I is a preferred embodiment of the orally administered composition, excluding inactive ingredients, as used in the inventive methods. The amounts recited in Table I represent the preferred dosage of the ingredients listed.

TABLE I

| Herb | Type Of Extract | Plant Part | Amount (mg) |
| --- | --- | --- | --- |
| Rosemary | supercritical | leaf | 100 |
| Rosemary | hydroalcoholic (23% TPA - 34.5 mg) | leaf | 50 |
| Turmeric | supercritical (45% turmerones - 4.5 mg) | rhizome | 10 |
| Turmeric | hydroalcoholic (7% curcumin - 7 mg) | rhizome | 100 |
| Ginger | supercritical (30% pungent compounds - 16.2 mg 8% zingiberene - 4.3 mg) | rhizome | 54 |
| Ginger | hydroalcoholic (3% pungent compounds - 1.4 mg) | rhizome | 46 |
| Holy basil | hydroalcoholic (2% ursolic acid - 2 mg) | leaf | 100 |
| Green tea | hydroalcoholic (45% polyphenols - 45 mg) | leaf | 100 |
| Huzhang | hydroalcoholic (8% resveratrol - 6.4 mg) | root & rhizome | 80 |
| Chinese Goldthread | hydroalcoholic (6% berberine - 2.4 mg) | root | 40 |
| Barberry | hydroalcoholic (6% berberine - 2.4 mg) | root | 40 |
| Oregano | supercritical (0.8% TPA - 0.32 mg) | leaf | 40 |
| Scutellaria Baicalensis | hydroalcoholic (5:1) | root | 20 |

Preferably, the composition set forth in Table I also includes extra virgin olive oil and yellow beeswax.

The inventive methods use a therapeutically effective amount of the active compositions indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the present inventive subject matter.

The inventive methods use compositions which are preferably delivered to the patient by means of a pharmaceutically acceptable carrier. Such carriers are well known in the art and generally will be in either solid or liquid form. Solid form pharmaceutical preparations which may be prepared according to the present inventive subject matter include powders, tablets, dispersible granules, capsules, and cachets. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the inventive subject matter may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the present inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857–884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

It is not expected that the inventive methods use compositions which will display significant adverse interactions with other synthetic or naturally occurring substances. Thus, a compound of the present inventive subject matter may be administered in combination with other compounds and compositions useful for treating prostate neoplasia. In particular the inventive methods use compositions which may be administered in combination with other inventive compositions, other antineoplastic substances, and the like.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435–1712, which is hereby incorporated by reference in its entirety. Such formulations may influence the physical state, stability, rate of in vivo release, and rate of in vivo clearance of the present therapeutic agents of the inventive subject matter.

Route(s) of Administration

The compounds and compositions are preferably administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule, to further enhance stability and provide release in the intestinal tract to improve absorption, is the best mode of administration currently contemplated.

Dosage

Dosage levels on the order of about 0.001 mg to about 100 mg per kilogram body weight of the active ingredient compounds or compositions are useful in the treatment of the above conditions, with preferred levels ranging from 200 mg per day to 1600 mg per day. The compounds and compositions of the present inventive subject matter may usually be given in two or three doses daily. Starting with a low dose (200–300 mg) twice daily and slowly working up to higher doses if needed is a preferred strategy. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

EXAMPLES

The following examples are illustrative of the present inventive subject matter and are not intended to be limitations thereon. Unless otherwise indicated, all percentages are based upon 100% by weight of the final composition.

Example 1

Preparation of the Inventive Compositions

The inventive compositions are prepared by methods known in the art, and disclosed in Applicants' U.S. Pat. No. 6,387,416. The preparation of the component elements of the inventive compositions is summarized as follows:

The hydroalcoholic extract of ginger used in the inventive compositions is preferably prepared as follows. The ginger rhizome, which is preferably cryogenically ground to preserve heat sensitive components, is subjected to supercritical extraction to obtain: (i) an oil extract, referred to herein as "the supercritical extract" of ginger, containing delicate lipophilic components, and (ii) an oil-free residue. The oil-free residue is then extracted in a water/alcohol, preferably water/ethanol, mixture composed of 60–80 parts alcohol and 40–20 parts water. The alcohol/water liquid is then evaporated off, leaving a powdered extract residue, referred to herein as "the hydroalcoholic extract" of ginger.

The composition of this invention will preferably contain the supercritical extract and the hydroalcoholic extract of ginger at a weight ratio of preferably from about 0.9 to about 1.4 parts, more preferably from about 1.1 to about 1.3 parts, most preferably about 1.17 parts, of supercritical extract per 1 part post-supercritical hydroalcoholic extract.

The supercritical extracts of ginger, rosemary, turmeric and oregano used in the inventive compositions can be prepared according to known supercritical extraction methods, such as disclosed, e.g., in E. Stahl, K. W. Quirin, D. Gerard, Dense Gases for Extraction and Refining, Springer Verlag 4 1988, which is hereby incorporated by reference herein.

The hydroalcoholic extracts of rosemary, turmeric, holy basil, green tea, huzhang, Chinese goldthread, barberry and *Scutellaria baicalensis* used in the inventive compositions can be prepared according to conventional hydroalcoholic extraction techniques. For example, the hydroalcoholic extracts can be prepared by extracting the plant portion in a water/alcohol (preferably water/ethanol) mixture (preferably composed of 60–80 parts alcohol and 40–20 parts water), and then evaporating off the water/alcohol liquid, leaving a powdered extract residue (referred to herein as "the hydroalcoholic extract").

In the composition of this invention, the hydroalcoholic extract of turmeric and the supercritical extract of turmeric will preferably be present at a weight ratio of preferably from about 8 to about 12 parts, more preferably from about 9 parts to about 11 parts, most preferably about 10 parts, of hydroalcoholic extract per 1 part of supercritical extract.

The composition of this invention will preferably contain the supercritical extract of rosemary and the hydroalcoholic extract of rosemary at a weight ratio of preferably from about 1.6 to about 2.4 parts, more preferably from about 1.8 to about 2.2 parts, most preferably about 2.0 parts, of supercritical extract per 1 part of hydroalcoholic extract.

The hydroalcoholic extract of ginger used in the inventive compositions will preferably contain from about 2.4% to about 3.6%, more preferably from about 2.7% to about 3.3%, most preferably about 3.0%, by weight of pungent compounds (e.g., shogaol).

The supercritical extract of ginger used in the inventive compositions will contain preferably from about 24% to about 36%, more preferably from about 27% to about 33%, most preferably about 30%, by weight of pungent compounds (e.g., shogaol) and preferably from about 6.4% to about 9.6%, more preferably from about 7.2% to about 8.8%, most preferably about 8%, by weight of zingiberene.

The supercritical extract of turmeric used in the inventive compositions will contain preferably from about 36% to about 54%, more preferably from about 40.5% to about 49.5%, most preferably about 45%, by weight of turmerones.

The supercritical extract of rosemary used in the inventive compositions will contain preferably from about 18.4% to about 27.6%, more preferably from about 20.7% to about 25.3%, most preferably about 23%, by weight of total phenolic antioxidants ("TPA").

The supercritical extract of oregano used in the inventive compositions will contain preferably from about 0.64% to about 0.96%, more preferably from about 0.72% to about 0.88%, most preferably about 0.8%, by weight of TPA.

The hydroalcoholic extract of turmeric used in the inventive compositions will contain preferably from about 5.6% to about 8.4%, more preferably from about 6.3% to about 7.7%, most preferably about 7%, by weight of curcumin.

The hydroalcoholic extract of rosemary used in the inventive compositions will contain preferably from about 18.4% to about 27.6%, more preferably from about 20.7% to about 25.3%, most preferably about 23%, by weight of TPA.

The hydroalcoholic extract of holy basil used in the inventive compositions will contain preferably from about 1.6% to about 2.4%, more preferably from about 1.8% to about 2.2%, most preferably about 2%, by weight of ursolic acid.

The hydroalcoholic extract of green tea used in the inventive compositions will contain preferably from about 36% to about 54%, more preferably from about 40.5% to about 49.5%, most preferably about 45%, by weight of polyphonies.

The hydroalcoholic extract of huzhang used in the inventive compositions will contain preferably from about 6.4% to about 9.6%, more preferably from about 7.2% to about 8.8%, most preferably about 8%, by weight of resveratrol.

The hydroalcoholic extract of Chinese goldthread used in the inventive compositions will contain preferably from about 4.8% to about 7.2%, more preferably from about 5.4% to about 6.6%, most preferably about 6%, by weight of berberine.

The hydroalcoholic extract of barberry used in the inventive compositions will contain preferably from about 4.8% to about 7.2%, more preferably from about 5.4% to about 6.6%, most preferably about 6%, by weight of berberine.

Example 2

Effect of the Inventive Compositions on Prostate Cancer Cells

A series of dilutions of the inventive composition in DMSO were prepared, and the dilutions were added to LNCaP growth medium so that all doses tested had equivalent (0.1%) DMSO levels. Cell growth curves were prepared by counting cells at 24, 48, and 72 hours, and were compared to control cells treated at the same times with 0.1% DMSO alone. Apoptosis in these cultures was evaluated by Western blot analysis of PARP cleavage and measurement of caspase-3 activity using a calorimetric substrate assay. Effects on purified COX-2 enzyme activity was measured using a calorimetric assay, and effects on COX-2 protein expression was determined via Western blot analysis of protein extracts from treated cells. Activities were also compared to the effects of purified curcumin dissolved in DMSO, at levels equivalent to those that would be found in the inventive compositions at similar doses.

Figure 1:
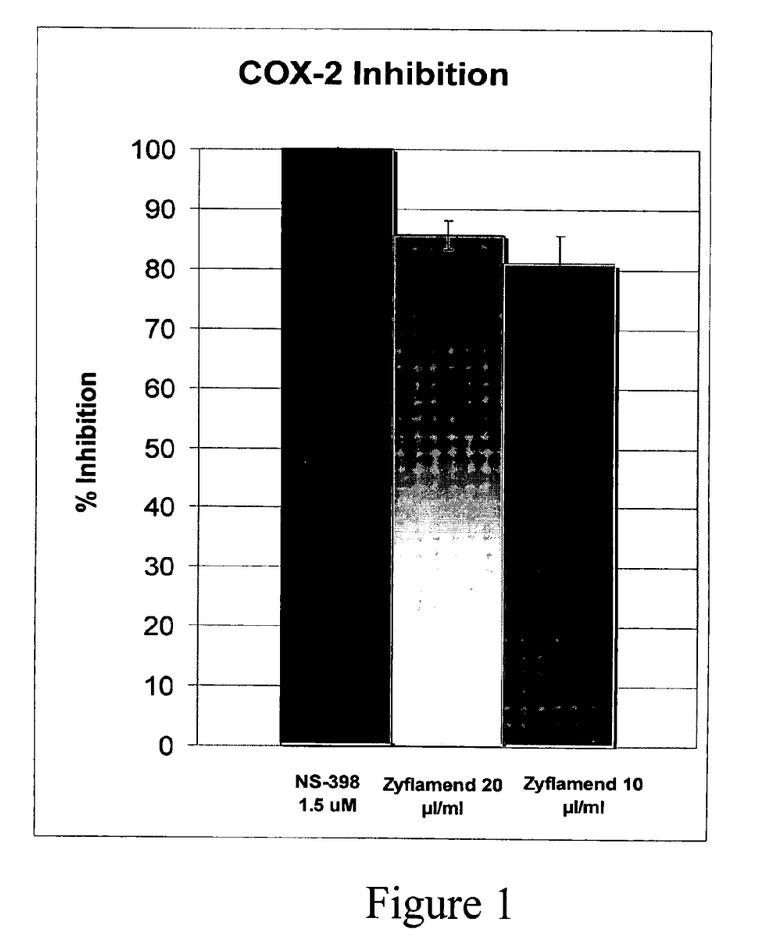
FIG. 1 is a graph which depicts COX-2 inhibition produced by the inventive compositions.
Figure 2:
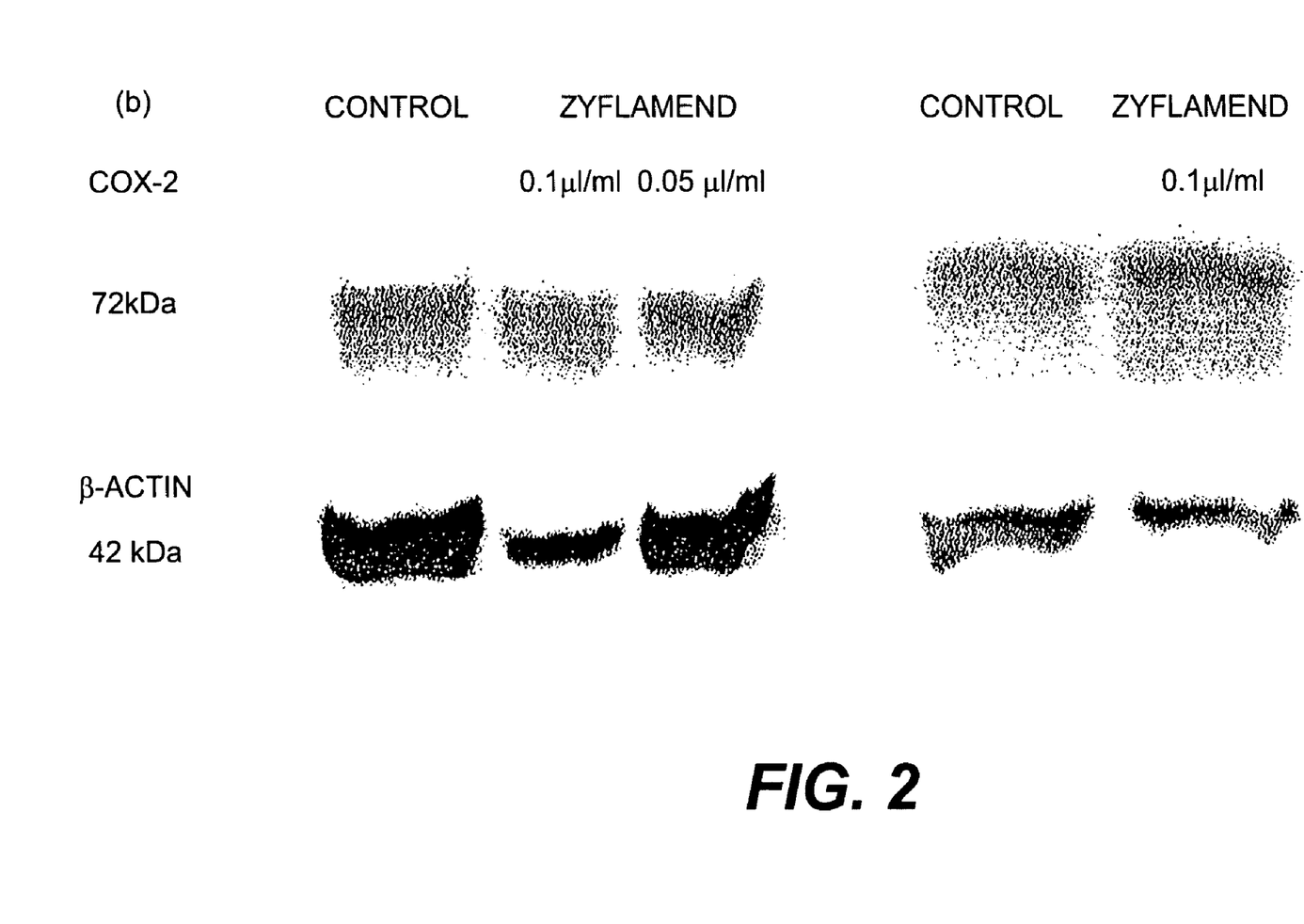
FIG. 2 is a photograph which depicts a Western blot of COX-s expression in LNCaP cells following treatment with the inventive compositions.
Figure 3:
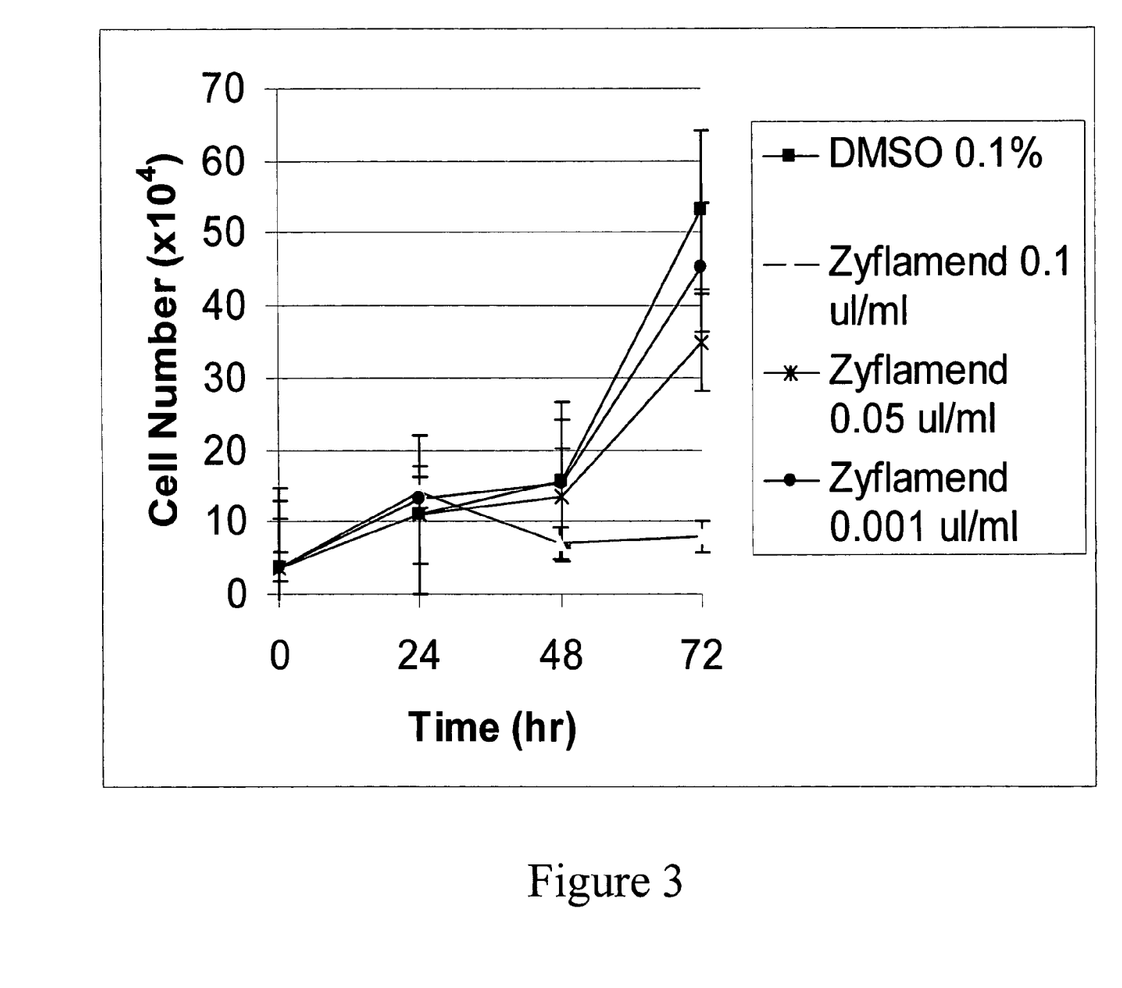
FIG. 3 is a graph which depicts the growth-inhibitory effects of the inventive compositions on LNCaP cells.
Figure 4:
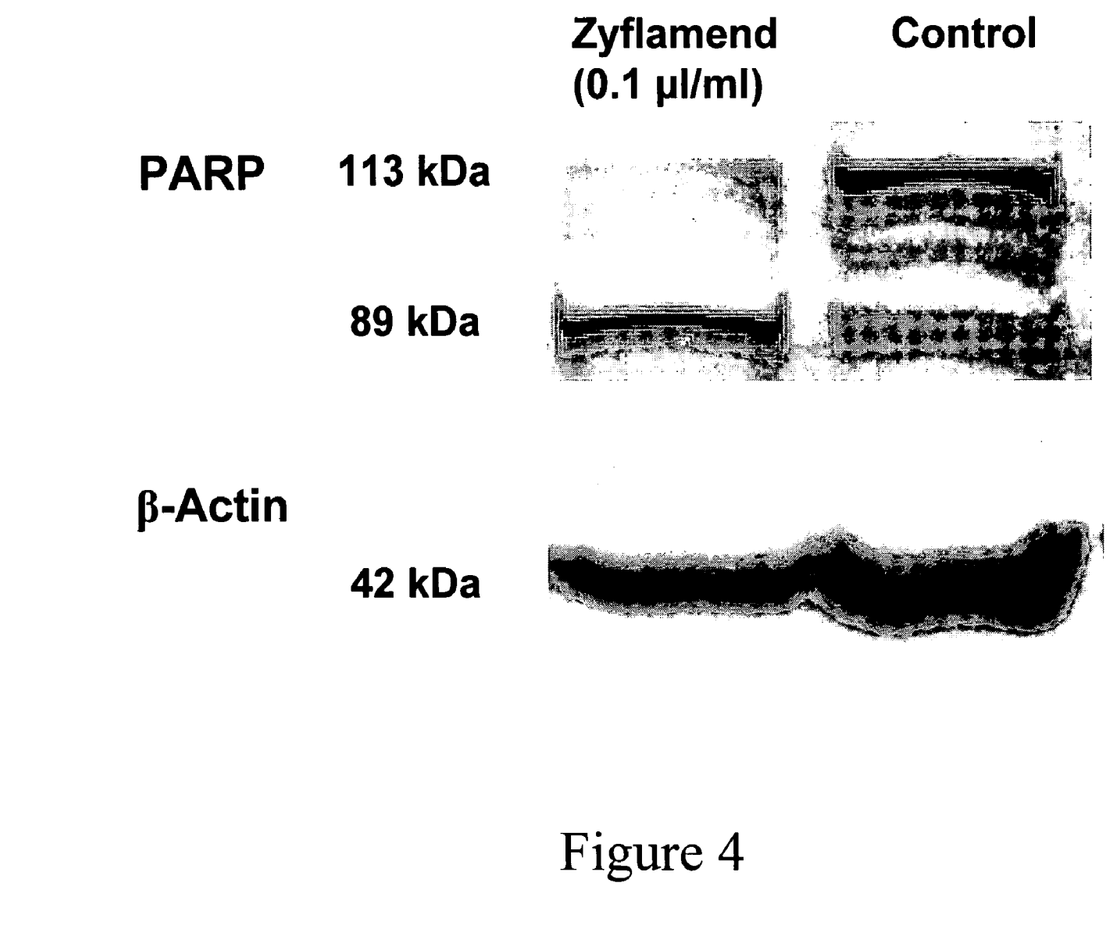
FIG. 4 is a photograph which depicts a Western blot of PARP cleavage fragments produced by treatment of LNCaP cells with the inventive compositions.
Figure 5:
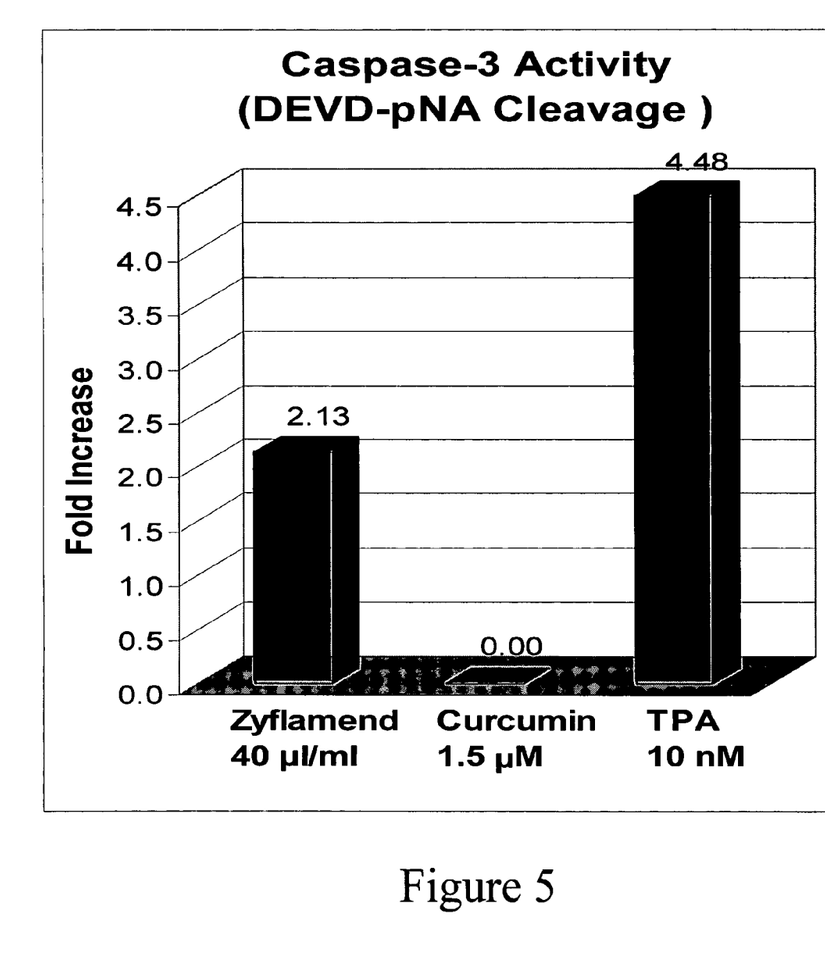
FIG. 5 is a graph which depicts Caspase-3 activity in LNCaP cells following treatment with the inventive compositions.

LNCaP cell growth was suppressed by the inventive compositions, and by 72 hours there was a 78% reduction in cell number in treated cultures ($7.9 \times 10^4$ vs $3.53 \times 10^5$ cells per well, p=0.01) compared to controls. PARP cleavage fragments were evident and caspase-3 activity was upregulated 2-fold by 72 hour treatment, demonstrating an apoptotic effect that was not found in controls. COX-2 activity was also significantly decreased in the presence of the inventive compositions, while equivalent doses of curcumin alone did not inhibit COX-2 in the assay utilized. COX-2 protein expression in LNCaP cells was not affected. The results are of this example are shown in FIGS. 1-5.

These results demonstrate that the inventive compositions strongly suppress LNCaP cells and induce apoptosis. These effects appear to be more potent that those observed with curcumin alone, demonstrating a synergistic effect between the extracts used in the inventive compositions.

Example 3

Effect of the Inventive Compositions on Pre-malignant Prostate Neoplasia

A patient presents for treatment of a pre-malignant neoplasia of the prostate. An inventive composition is administered to said patient over a course of treatment lasting for several weeks, resulting in no significant side effects. The patient experiences a reversal in the growth of neoplastic cells and death of existing neoplastic cells, resulting in the neoplasia becoming undetectable.

Example 4

Effect of the Inventive Compositions on Prostate Epithelioma

A patient presents for treatment of a malignant stage B epithelioma of the prostate, confirmed by elevated PSA test, manual examination, and biopsy of the tumor. An inventive composition is administered to said patient over a course of treatment lasting for several months, resulting in no significant side effects. The patient experiences a reversal in the growth rate of tumor cells, death of existing tumor cells and reduction in tumor size, and no metastasis of the tumor. With continuing treatment, the patient continues to exhibit no secondary symptoms of prostate neoplasia, no long term side effects of the treatment, and no metastasis of the tumor.

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

We claim:

1. A method for treating prostate neoplasia in a subject, comprising the step of administering an effective amount of a composition to said subject to treat said prostate neoplasia, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry, provided that said prostate neoplasia is not prostatic intraepithelial neoplasia.

2. The method of claim 1, wherein said composition is administered orally.

3. The method of claim 2, wherein the orally administered composition is in the form of one or more capsules, one or more tablets, or one or more pills.

4. The method of claim 1, wherein the composition comprises:

(A) from about 4.5% to about 7.5% by weight of the hydroalcoholic extract of ginger;
(B) from about 5.5% to about 8.5% by weight of the supercritical extract of ginger;
(C) from about 1.0% to about 1.5% by weight of the supercritical extract of turmeric;
(D) from about 10.0% to about 16.0% by weight of the supercritical extract of rosemary;

(E) from about 4.0% to about 6.0% by weight of the supercritical extract of oregano;
(F) from about 10.0% to about 16.0% by weight of the hydroalcoholic extract of turmeric; (0) from about 5.5% to about 8.0% by weight of the hydroalcoholic extract of rosemary;
(H) from about 10.0% to about 16.0% by weight of the hydroalcoholic extract of holy basil;
(I) from about 10.0% to about 16.0% by weight of the hydroalcoholic extract of green tea;
(J) from about 8.0% to about 12.0% by weight of the hydroalcoholic extract of huzhang;
(K) from about 4.0% to about 6.0% by weight of the hydroalcoholic extract of Chinese goldthread;
(L) from about 4.0% to about 6.0% by weight of the hydroalcoholic extract of barberry; and
(M) from about 2.0% to about 3.0% by weight of the hydroalcoholic extract of *Scutellaria baicalensis*.

5. The method of claim 1, wherein the weight ratio of the supercritical extract of ginger to the hydroalcoholic extract of ginger is from about 0.9:1 to about 1.4:1.

6. The method of claim 1, wherein the weight ratio of the hydroalcoholic extract of turmeric to the supercritical extract of turmeric is from about 8:1 to about 12:1.

7. The method of claim 1, wherein the weight ratio of the supercritical extract of rosemary to the hydroalcoholic extract of rosemary is from about 1.6:1 to about 2.4:1.

8. The method of claim 1, wherein the hydroalcoholic extract of ginger comprises from about 2.4% to about 3.6% by weight of pungent compounds.

9. The method of claim 1, wherein the superoritical extract of ginger comprises from about 24% to about 36% by weight of pungent compounds and from about 6.4% to about 9.6% by weight of zingiberene.

10. The method of claim 1, wherein the supercritical extract of turmeric comprises from about 36% to about 54% by weight of turmerones.

11. The method of claim 1, wherein the supercritical extract of rosemary comprises from about 18.4% to about 27.6% by weight of total phenolic antioxidants.

12. The method of claim 1, wherein the supercritical extract of oregano comprises from about 0.64% to about 0.96% by weight of total phenolic antioxidants.

13. The method of claim 1, wherein the hydroalcoholic extract of turmeric comprises from about 5.6% to about 8.4% by weight of curcumin.

14. The method of claim 1, wherein the hydroalcoholic extract of rosemary comprises from about 18.4% to about 27.6% by weight of total phenolic antioxidants.

15. The method of claim 1, wherein the hydroalcoholic extract of holy basil comprises from about 1.6% to about 2.4% by weight of ursolic acid.

16. The method of claim 1, wherein the hydroalcoholic extract of green tea comprises from about 36% to about 54% by weight of polyphenols.

17. The method of claim 1, wherein the hydroalcoholic extract of huzhang comprises from about 6.4% to about 9.6% by weight of resveratrol.

18. The method of claim 1, wherein the hydroalcoholic extract of Chinese goldthread comprises from about 4.8% to about 7.2% by weight of berberine.

19. The method of claim 1, wherein the hydroalcoholic extract of barberry comprises from about 4.8% to about 7.2% by weight of berberine.

20. The method of claim 1, wherein said composition provided in step (a) comprises:

(A) from about 4.5% to about 7.5% by weight of the hydroalcoholic extract of ginger, wherein the extract comprises from about 2.4% to about 3.6% by weight of pungent compounds;
(B) from about 5.5% to about 8.5% by weight of the supercritical extract of ginger, wherein the extract comprises from about 24% to about 36% by weight of pungent compounds and from about 6.4% to about 9.6% by weight of zingiberene;
(C) from about 1.0% to about 1.5% by weight of the supercritical extract of turmeric, wherein the extract comprises from about 36% to about 54% by weight of turmerones;
(D) from about 10.0% to about 16.0% by weight of the supercritical extract of rosemary, wherein the extract comprises from about 18.4% to about 27.6% by weight of total phenolic antioxidants;
(E) from about 4.0% to about 6.0% by weight of the supercritical extract of oregano, wherein the extract comprises from about 0.64% to about 0.96% by weight of total phenolic antioxidants;
(F) from about 10.0% to about 16.0% by weight of the hydroalcoholic extract of turmeric, wherein the extract comprises from about 5.6% to about 8.4% by weight of curcumin;
(G) from about 5.5% to about 8.0% by weight of the hydroalcoholic extract of rosemary, wherein the extract comprises from about 18.4% to about 27.6% by weight of total phenolic antioxidants;
(H) from about 10.0% to about 16.0% by weight of the hydroalcoholic extract of holy basil, wherein the extract comprises from about 1.6% to about 2.4% by weight of ursolic acid;
(I) from about 10.0% to about 16.0% by weight of the hydroalcoholic extract of green tea, wherein the extract comprises from about 36% to about 54% by weight of polyphenols;
(J) from about 8.0% to about 12.0% by weight of the hydroalcoholic extract of huzhang, wherein the extract comprises from about 6.4% to about 9.6% by weight of resveratrol;
(K) from about 4.0% to about 6.0% by weight of the hydroalcoholic extract of Chinese goldthread, wherein the extract from about 4.8% to about 7.2% by weight of berberine;
(L) from about 4.0% to about 6.0% by weight of the hydroalcoholic extract of barberry, wherein the extract from about 4.8% to about 7.2% by weight of berberine; and
(M) from about 2.0% to about 3.0% by weight of the hydroalcoholic extract of *Scutellaria baicalensis;*
and wherein said composition further comprises:
(i) the supercritical extract of ginger and the hydroalcoholic extract of ginger at a weight ratio of from about 0.9 to about 1.4 parts of supercritical extract per 1 part of post supercritical hydroalcoholic extract;
(ii) the hydroalcoholic extract of turmeric and the supercritical extract of turmeric at a weight ratio of from about 8 to about 12 parts of hydroalcoholic extract per 1 part of supercritical extract; and
(iii) the supercritical extract of rosemary and the hydroalcoholic extract of rosemary at a weight ratio of from about 1.6 to about 2.4 parts of supercritical extract per 1 part of hydroalcoholic extract.

21. The method of claim 1, said composition is administered in a daily dosage of at least about 700 mg.

22. The method of claim 1, wherein said composition is administered on a daily basis for at least 4 weeks.

23. A method for treating at least one cancerous tumor of the prostate in a subject, comprising the step of administering an effective amount of a composition to said subject to treat said tumor, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

24. The method of claim 23, wherein said composition is administered orally.

25. The method of claim 24, wherein the orally administered composition is in the form of one or more capsules, one or more tablets, or one or more pills.

26. The method of claim 23, wherein the composition comprises:
(A) from about 4.5% to about 7.5% by weight of the hydroalcoholic extract of ginger;
(B) from about 5.5% to about 8.5% by weight of the supercritical extract of ginger;
(C) from about 1.0% to about 1.5% by weight of the supercritical extract of turmeric;
(D) from about 10.0% to about 16.0% by weight of the supercritical extract of rosemary;
(E) from about 4.0% to about 6.0% by weight of the supercritical extract of oregano;
(F) from about 10.0% to about 16.0% by weight of the hydroalcoholic extract of turmeric;
(G) from about 5.5% to about 8.0% by weight of the hydroalcoholic extract of rosemary;
(H) from about 10.0% to about 16.0% by weight of the hydroalcoholic extract of holy basil;
(I) from about 10.0% to about 16.0% by weight of the hydroalcoholic extract of green tea;
(J) from about 810% to about 12.0% by weight of the hydroalcoholic extract of huzhang;
(K) from about 4.0% to about 6.0% by weight of the hydroalcoholic extract of Chinese goldthread;
(L) from about 4.0% to about 6.0% by weight of the hydroalcoholic extract of barberry; and
(M) from about 2.0% to about 3.0% by weight of the hydroalcoholic extract of *Scutellaria baicalensis*.

27. The method of claim 23, wherein said at least one cancerous tumor is detected during surgery on the prostate of said subject, having not been felt by a physician on physical examination of said subject.

28. The method of claim 23, wherein said at least one cancerous tumor is confined to the prostate of said subject and is detected by a physician on physical examination of said subject.

29. The method of claim 23, wherein cancer related to said at least one cancerous tumor extends beyond the prostate capsule of said subject, but has not spread to lymph nodes in said subject.

30. The method of claim 23, wherein cancer related to said at least one cancerous tumor is metastasized to regional lymph nodes or other parts of said subject.

31. A method for treating side effects associated with prostate neoplasia in a subject, comprising the step of administering an effective amount of a composition to said subject to treat said side effects, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry,
wherein said side effects are selected from the group consisting of disrupted sexual desire or performance on either a temporary or permanent basis, impotence, extensive monitoring for progression of the disease, stress of illness, and urinary incontinence.

32. The method of claim 31, wherein said composition is administered orally.

33. The method of claim 32, wherein the orally administered composition is in the form of one or more capsules, one or more tablets, or one or more pills.

34. The method of claim 31, wherein the composition comprises:
(A) from about 4.5% to about 7.5% by weight of the hydroalcoholic extract of ginger;
(B) from about 5.5% to about 8.5% by weight of the supercritical extract of ginger;
(C) from about 1.0% to about 1.5% by weight of the supercritical extract of turmeric;
(D) from about 10.0% to about 16.0% by weight of the supercritical extract of rosemary;
(E) from about 4.0% to about 6.0% by weight of the supercritical extract of oregano;
(F) from about 10.0% to about 16.0% by weight of the hydroalcoholic extract of turmeric;
(G) from about 5.5% to about 8.0% by weight of the hydroalcoholic extract of rosemary;
(H) from about 10.0% to about 16.0% by weight of the hydroalcoholic extract of holy basil;
(I) from about 10.0% to about 16.0% by weight of the hyciroalcoholic extract of green tea;
(J) from about 8.0% to about 12.0% by weight of the hydroalcoholic extract of huzhang;
(K) from about 4.0% to about 6.0% by weight of the hydroalcoholic extract of Chinese goldthread;
(L) from about 4.0% to about 6.0% by weight of the hydroalcoholic extract of barberry; and
(M) from about 2.0% to about 3.0% by weight of the hydroalcoholic extract of *Scutellaria baicalensis*.

35. The method of claim 31, wherein said side effect treated comprises disrupted sexual performance.

* * * * *